(12) United States Patent
Bourcet

(10) Patent No.: US 10,283,720 B2
(45) Date of Patent: May 7, 2019

(54) COMPOUND, COMPOSITION AND ORGANIC LIGHT-EMITTING DEVICE

(71) Applicants: Cambridge Display Technology Limited, Godmanchester (GB); Sumitomo Chemical Company Limited, Tokyo (JP)

(72) Inventor: Florence Bourcet, Godmanchester (GB)

(73) Assignees: Cambridge Display Technology Limited, Godmanchester (GB); Sumitomo Chemical Company Limited, Tokyo (JP)

( * ) Notice: Subject to any disclaimer, the term of this patent is extended or adjusted under 35 U.S.C. 154(b) by 536 days.

(21) Appl. No.: 14/602,670

(22) Filed: Jan. 22, 2015

(65) Prior Publication Data

US 2015/0214493 A1 Jul. 30, 2015

(30) Foreign Application Priority Data

Jan. 24, 2014 (GB) .................... 1401245.4

(51) Int. Cl.
| C09K 11/06 | (2006.01) |
| H01L 51/00 | (2006.01) |
| H01L 51/50 | (2006.01) |
| C07D 409/04 | (2006.01) |
| C07D 409/14 | (2006.01) |

(52) U.S. Cl.
CPC ........ *H01L 51/0073* (2013.01); *C07D 409/04* (2013.01); *C07D 409/14* (2013.01); *C09K 11/06* (2013.01); *H01L 51/0074* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *C09K 2211/1096* (2013.01); *H01L 51/0085* (2013.01); *H01L 51/5016* (2013.01)

(58) Field of Classification Search
CPC .... C07D 409/04; C07D 409/14; C09K 11/06; C09K 2211/1007; C09K 2211/1011; C09K 2211/1029; C09K 2211/1044; C09K 2211/1088; C09K 2211/1092; C09K 2211/1096; H01L 51/0073; H01L 51/0074; H01L 51/0085; H01L 51/5016
See application file for complete search history.

(56) References Cited

U.S. PATENT DOCUMENTS

| 3,820,993 | A | 6/1974 | Lewis et al. | |
| 2003/0152801 | A1* | 8/2003 | Liao | H01L 51/5092 |
| | | | | 428/690 |
| 2004/0076853 | A1* | 4/2004 | Jarikov | C09K 11/06 |
| | | | | 428/690 |
| 2005/0069728 | A1* | 3/2005 | Ragini | C07F 15/0033 |
| | | | | 428/690 |
| 2005/0069729 | A1* | 3/2005 | Ueda | H01L 51/005 |
| | | | | 428/690 |
| 2006/0134538 | A1* | 6/2006 | Radu | C07D 311/82 |
| | | | | 430/58.15 |
| 2007/0009759 | A1* | 1/2007 | Burn | C07F 15/0033 |
| | | | | 428/690 |
| 2012/0085997 | A1* | 4/2012 | Sugita | C07D 471/04 |
| | | | | 257/40 |
| 2013/0221340 | A1* | 8/2013 | Kamatani | C07D 335/16 |
| | | | | 257/40 |

FOREIGN PATENT DOCUMENTS

| EP | 1506959 A2 | 2/2005 |
| KR | 2013/0067282 Z | 6/2013 |
| WO | WO 2014/010823 A1 | 1/2014 |

OTHER PUBLICATIONS

Strohriegl et al., Novel host materials for blue phosphorescent OLEDs. Proc. SPIE 8829, Organic Light Emitting Materials and Devices XVII. 2013; 8829. 12 pages.

(Continued)

*Primary Examiner* — Dawn L Garrett
(74) *Attorney, Agent, or Firm* — Wolf, Greenfield & Sacks, P.C.

(57) ABSTRACT

A compound of formula (I)

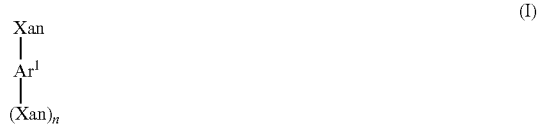

wherein:
Ar$^1$ represents an aryl or heteroaryl group that may be unsubstituted or substituted with one or more substituents;
n is 0 or 1; and
Xan independently in each occurrence represents a group selected from formula (IIa) or (IIb):

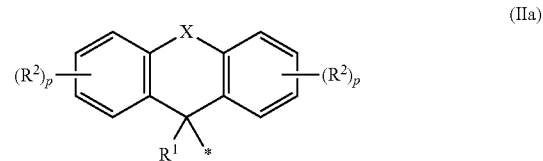

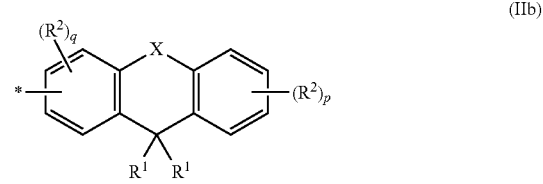

wherein X is O or S; R$^1$ independently in each occurrence is H or a substituent; R$^2$ independently in each occurrence is H or a substituent; p independently in each occurrence is 0, 1, 2, 3 or 4; q is 0, 1, 2 or 3; and * represents a bond to Ar$^1$. Use of compounds of formula (I) as a host for phosphorescent emitters is disclosed.

9 Claims, 1 Drawing Sheet

(56) References Cited

OTHER PUBLICATIONS

GB1401245.4, Jan. 24, 2014, Combined Search and Examination Report.
Sawicki et al, "Reaction of thiaxanthydrol with compound containing active hydrogen," Journal of Organic Chemistry, 1956, pp. 183-189.
Search Report from related application No. GB1401245.4, dated Jan. 24, 2014, pp. 1-7.

* cited by examiner

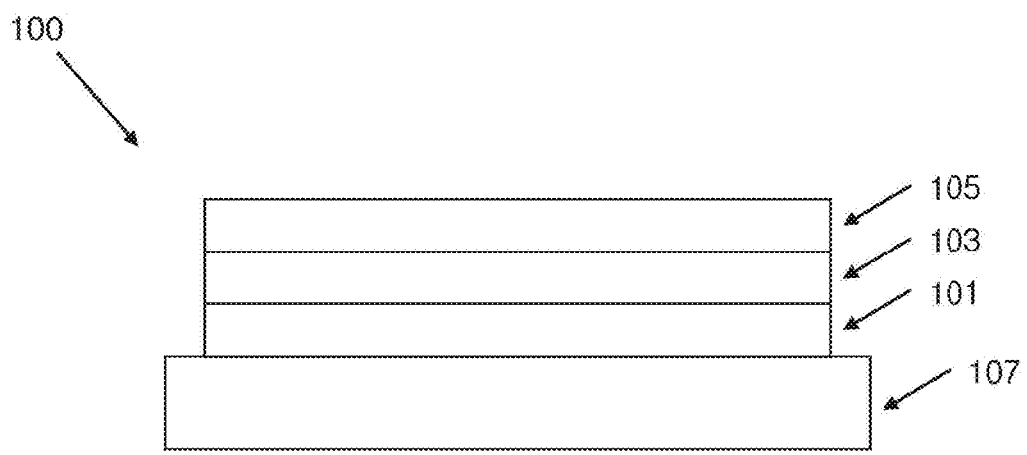

COMPOUND, COMPOSITION AND ORGANIC LIGHT-EMITTING DEVICE

RELATED APPLICATIONS

This application claims foreign priority benefits under 35 U.S.C. § 119(a)-(d) or 35 U.S.C. § 365(b) of British application number 1401245.4, filed Jan. 24, 2014, the entirety of which is herein incorporated by reference.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

Light-emitting materials include small molecule, polymeric and dendrimeric materials. Light-emitting polymers include poly(arylene vinylenes) such as poly(p-phenylene vinylenes) and polymers containing arylene repeat units, such as fluorene repeat units.

A light emitting layer may comprise a host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

Organic Electronics 13 (2012) 2741-2746 discloses use of the following spiro[fluorene-9,9'-xanthene]-based material as a host:

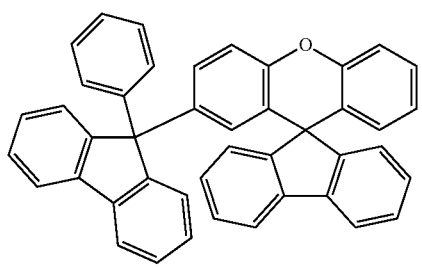 [SMILES: c1ccc(C2(c3ccc4c(c3)C3(c5ccccc5O4)c4ccccc4-c4ccccc43)c3ccccc3-c3ccccc32)cc1]

Sook et al, J. Mater. Chem., 2011, 21, 14604 discloses host materials DBT1, DBT2 and DBT3:

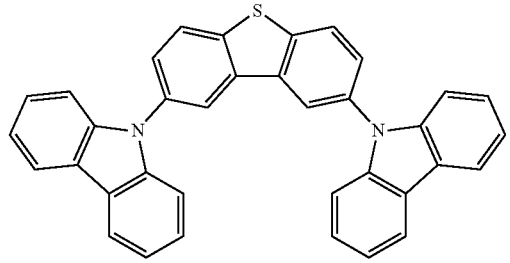

DBT1

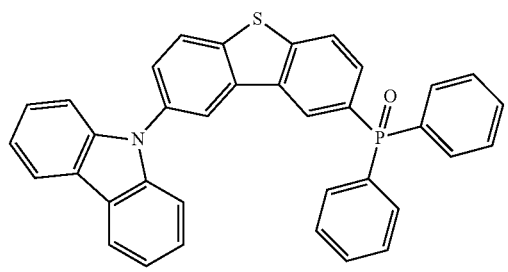

DBT2

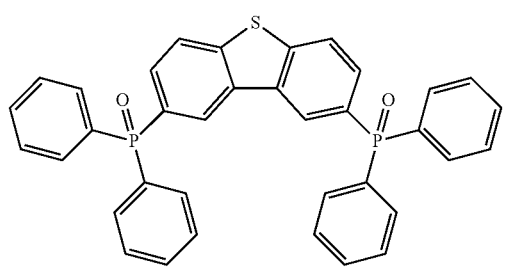

DBT3

SUMMARY OF THE INVENTION

In a first aspect the invention provides a compound of formula (I):

(I)

wherein:

$Ar^1$ represents an aryl or heteroaryl group that may be unsubstituted or substituted with one or more substituents;

n is 0 or 1; and

Xan independently in each occurrence represents a group selected from formula (IIa) or (IIb):

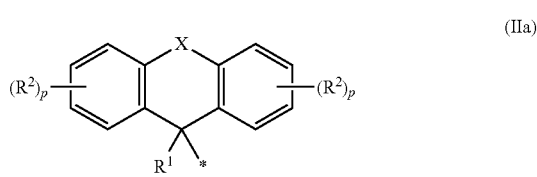

(IIa)

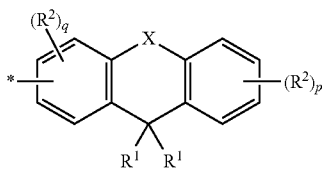

(IIb)

wherein X is O or S; $R^1$ independently in each occurrence is H or a substituent; $R^2$ independently in each occurrence is a substituent; p independently in each occurrence is 0, 1, 2, 3 or 4; q is 0, 1, 2 or 3; and * represents a bond to $Ar^1$.

In a second aspect the invention provides a composition comprising a compound according to the first aspect and at least one light-emitting dopant.

In a third aspect the invention provides a formulation comprising a compound according to the first aspect or a composition according to the second aspect and at least one solvent.

In a fourth aspect the invention provides an organic light-emitting device comprising an anode, a cathode and one or more organic layers between the anode and cathode including a light-emitting layer wherein at least one of the one or more organic layers comprises a compound according to the first aspect.

In a fifth aspect the invention provides a method of forming an organic light-emitting device according to the fourth aspect comprising the step of forming the light-emitting layer over one of the anode and the cathode and forming the other of the anode and the cathode over the light-emitting layer.

DESCRIPTION OF THE DRAWINGS

The invention will now be described in more detail with reference to the drawings in which:

The FIGURE illustrates an OLED according to an embodiment of the invention.

DETAILED DESCRIPTION OF THE INVENTION

The FIGURE illustrates an OLED 100 according to an embodiment of the invention comprising an anode 101, a cathode 105 and a light-emitting layer 103 between the anode and cathode. The device 100 is supported on a substrate 107, for example a glass or plastic substrate.

One or more further layers may be provided between the anode 101 and cathode 105, for example hole-transporting layers, electron transporting layers, hole blocking layers and electron blocking layers. The device may contain more than one light-emitting layer.

Preferred device structures include:
Anode/Hole-injection layer/Light-emitting layer/Cathode
Anode/Hole transporting layer/Light-emitting layer/Cathode
Anode/Hole-injection layer/Hole-transporting layer/Light-emitting layer/Cathode
Anode/Hole-injection layer/Hole-transporting layer/Light-emitting layer/Electron-transporting layer/Cathode.

Preferably, at least one of a hole-transporting layer and hole injection layer is present. Preferably, both a hole injection layer and hole-transporting layer are present.

Light-emitting materials include red, green and blue light-emitting materials.

A blue emitting material may have a photoluminescent spectrum with a peak in the range of 400-490 nm, optionally 420-490 nm.

A green emitting material may have a photoluminescent spectrum with a peak in the range of more than 490 nm up to 580 nm, optionally more than 490 nm up to 540 nm.

A red emitting material may optionally have a peak in its photoluminescent spectrum of more than 580 nm up to 630 nm, optionally 585-625 nm.

Light-emitting layer 103 may contain a compound of formula (I) doped with one or more luminescent dopants. The light-emitting layer 103 may consist essentially of these materials or may contain one or more further materials, for example one or more charge-transporting materials or one or more further light-emitting materials. When used as a host material for one or more light-emitting dopants, the lowest excited stated singlet ($S^1$) or the lowest excited state triplet ($T^1$) energy level of the host material is preferably no more than 0.1 eV below that of the light-emitting material, and is more preferably about the same as or higher than that of the light-emitting material in order to avoid quenching of luminescence from the light-emitting dopant.

In the case where the luminescent dopant is a phosphorescent dopant, the compound of formula (I) preferably has a $T^1$ of greater than 2.8 eV, preferably greater than 3.0 eV.

Triplet energy levels of compounds of formula (I) may be measured from the energy onset of the phosphorescence spectrum measured by low temperature phosphorescence spectroscopy (Y. V. Romaovskii et al, Physical Review Letters, 2000, 85 (5), p 1027, A. van Dijken et al, Journal of the American Chemical Society, 2004, 126, p 7718).

In a preferred embodiment, light-emitting layer 103 contains a compound of formula (I) and at least one of green and blue phosphorescent light-emitting materials.

Compounds of formula (I) in the case where n=1 may be selected from compounds of formulae (Ia), (Ib) and (Ic):

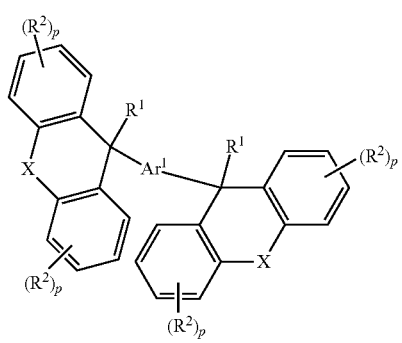

(Ia)

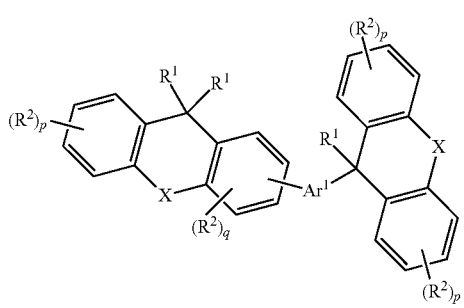

(Ib)

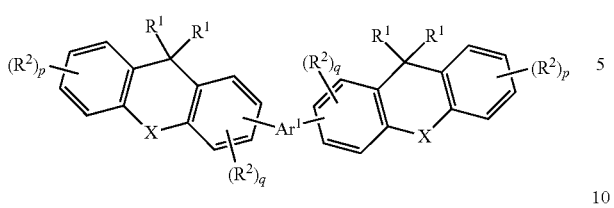
(Ic)

In compounds of formula (Ia) there is no conjugation between the two xanthene or thioxanthene groups, or between either of the xanthene or thioxanthene groups and $Ar^1$.

In compounds of formula (Ib) $Ar^1$ is conjugated to only one of the xanthene or thioxanthene groups.

In compounds of formula (Ic) $Ar^1$ may provide a conjugation path between both xanthene or thioxanthene groups.

The extent of conjugation of a compound of formula (I) may be controlled in order to control its lowest triplet excited state energy level. The extent of conjugation may be controlled by selection of a compound of formula (Ia), (Ib) and (Ic) and/or by selection of $Ar^1$.

$Ar^1$ is preferably a fused aromatic or heteroaromatic group.

In the case where n of formula (I) is 1, $Ar^1$ of formula (I) may be a group of formula (IIIa):

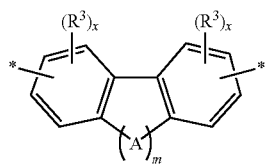
(IIIa)

wherein $R^3$ is the same or different in each occurrence and is a substituent; x independently in each occurrence is 0, 1, 2 or 3; and A independently in each occurrence is $NR^4$, $PR^4$, $—CR^4_2—$, $—SiR^4_2—$, O or S wherein $R^4$ is the same or different in each occurrence and is a substituent, m is 1, 2 or 3, the two groups $R^4$ of $—CR^4_2—$ or $—SiR^4_2—$ may be linked to form a ring, and * represents a point of attachment to a group Xan.

If m is greater than 1 then preferably each A is $CR^4_2$, or m−1 groups A are $CR^4_2$ and one group A is $NR^4$, $PR^4$, $—SiR^4_2—$, O or S.

Exemplary groups of formula (IIIa) include the following groups:

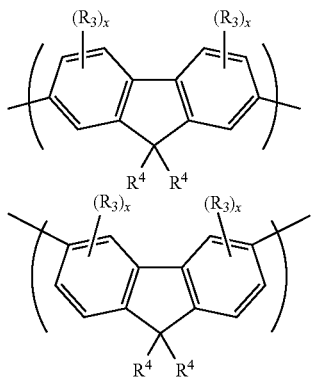

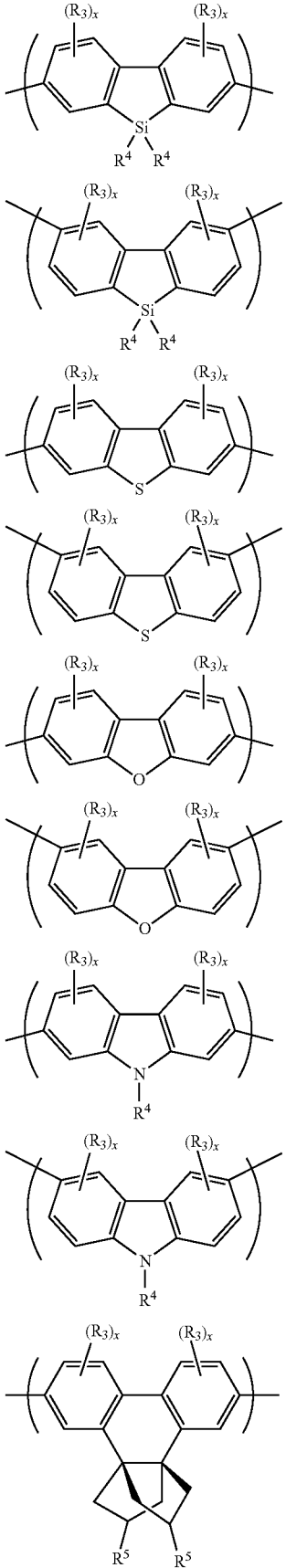

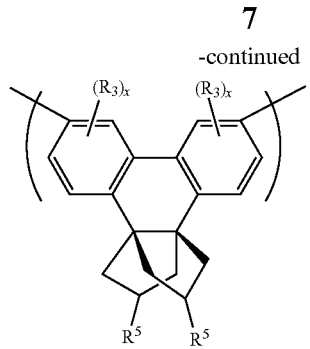

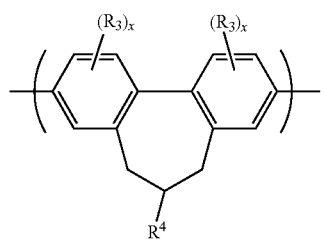

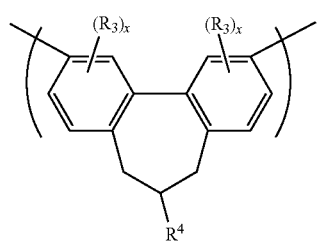

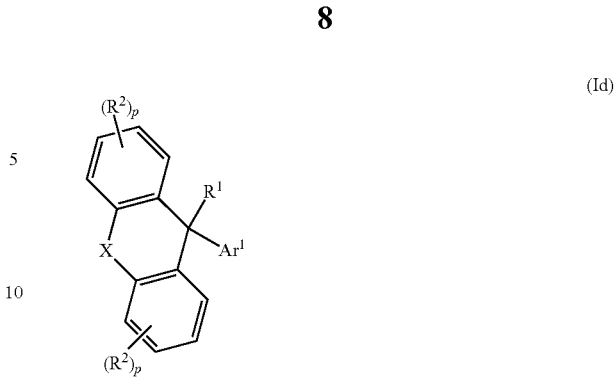

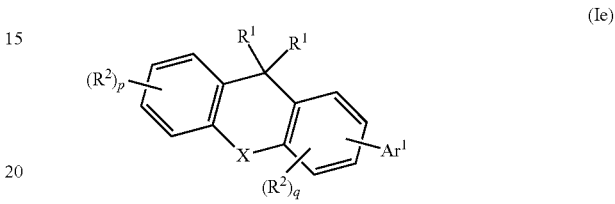

In the case of compounds of formula (Ic), $Ar^1$ may be selected to control the extent of conjugation between the two xanthene or thioxanthene groups. For example, a 3,6-linked group of formula (IIIa) may provide less conjugation between the two xanthene or thioxanthene groups than a 2,7-linked group of formula (IIIa).

By limiting or preventing conjugation between Ar1 and Xan of formula (I), for example as in compounds of formula (Ia), the HOMO and LUMO levels of the compound of formula (I) may be localized on $Ar^1$ and Xan.

In one embodiment, the LUMO of $Ar^1$ may be deeper (further from vacuum) than that of Xan. In this embodiment, $Ar^1$ may provide electron transport in the light-emitting layer.

In another embodiment, the HOMO of $Ar^1$ may be shallower (closer to vacuum) than that of Xan. In this embodiment, $Ar^1$ may provide hole transport in the light-emitting layer.

The extent of hole and/or electron transport provided by a compound of formula (I) may depend on the HOMO and LUMO levels of the compound of formula (I) relative to other compounds in the light-emitting layer. For example, a luminescent dopant may provide hole transport as well as light emission in a light-emitting layer.

By separating the HOMO and LUMO levels, a large $T^1$ value of the compound of formula (I) may be achieved without necessarily requiring a large $S^1$ value.

The compound of formula (I) may be selected from compounds of formulae 1(d) and 1(e):

$Ar^1$ of formula (Id) or (Ie) may be a group of formula (IIIb):

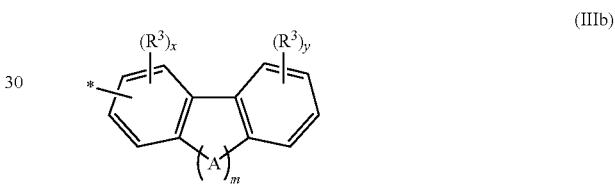

wherein $R^3$ is the same or different in each occurrence and is a substituent; x independently in each occurrence is 0, 1, 2 or 3; y is 0, 1, 2, 3 or 4; and A independently in each occurrence is $NR^4$, $PR^4$, $-CR^4_2-$, $-SiR^4_2$, O or S wherein $R^4$ is the same or different in each occurrence and is a substituent, m is 1, 2 or 3; the two groups $R^4$ of $CR^4_2$ or $SiR^4_2$ may be linked to form a ring, and * represents a point of attachment to Xan.

If m is greater than 1 then preferably each A is $CR^4_2$, or m−1 groups A are $CR^4_2$ and one group A is $NR^4$, $PR^4$, $-SiR^4_2-$, O or S.

Exemplary groups of formula (IIIb) include the following groups:

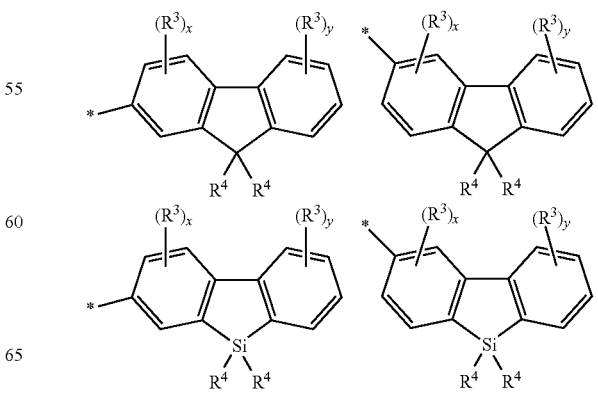

-continued

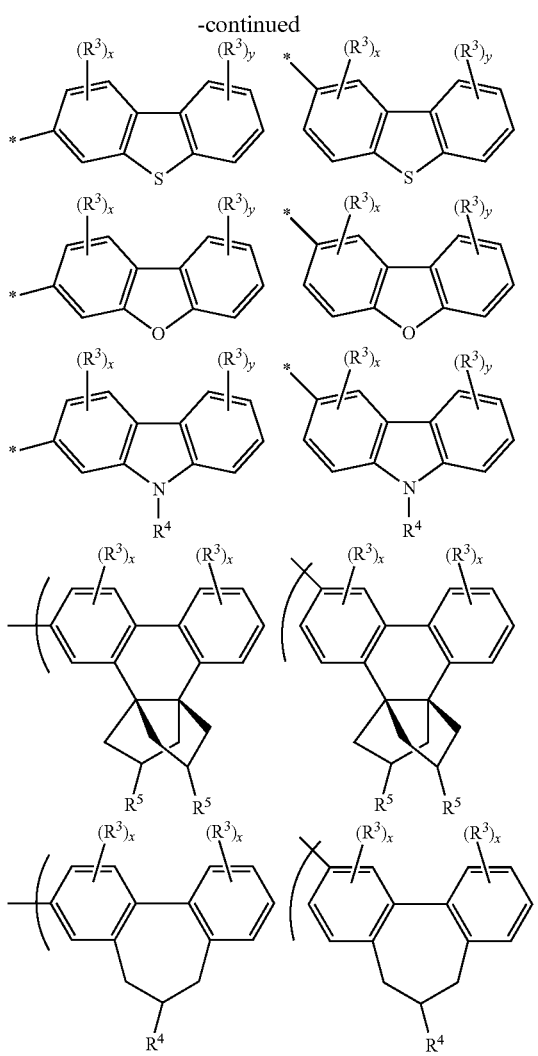

R¹ independently in each occurrence may be selected from the group consisting of: H;

CN;

alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F; and aryl and heteroaryl groups that may be unsubstituted or substituted with one or more substituents, preferably phenyl substituted with one or more $C_{1-20}$ alkyl groups.

Preferably, R¹ is a $C_{1-40}$ hydrocarbyl group.

Two groups R¹ linked to the same carbon atom are not linked to form a ring.

Each R² and R³, where present, may independently in each occurrence be selected from the group consisting of alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F; aryl and heteroaryl groups that may be unsubstituted or substituted with one or more substituents, preferably phenyl substituted with one or more $C_{1-20}$ alkyl groups; F; CN and $NO_2$.

R⁴ independently in each occurrence may be selected from the group consisting of:

H;

alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F; and aryl and heteroaryl groups that may be unsubstituted or substituted with one or more substituents, preferably phenyl substituted with one or more $C_{1-20}$ alkyl groups.

Preferably, R⁴ is a $C_{1-40}$ hydrocarbyl group.

Exemplary compounds of formula (I) include the following:

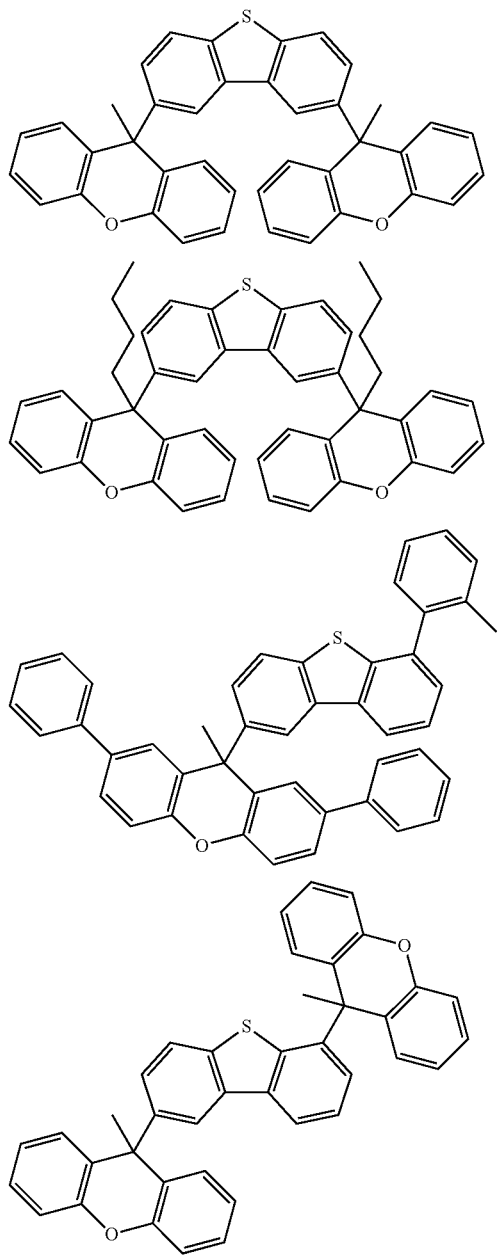

11
-continued
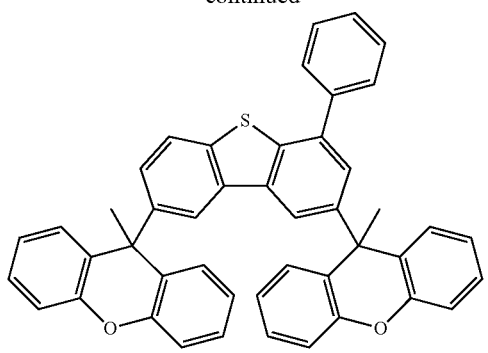
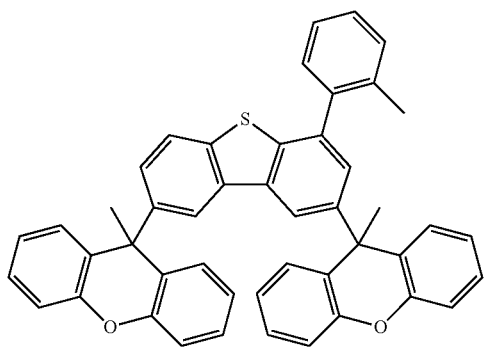
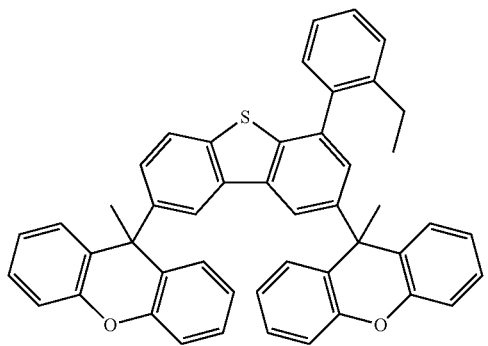
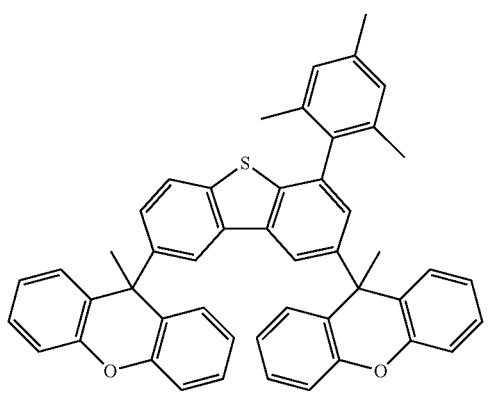
12
-continued
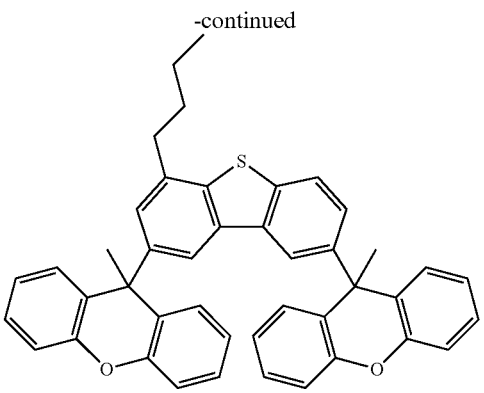
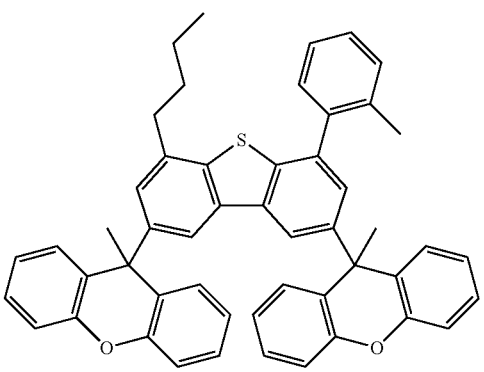
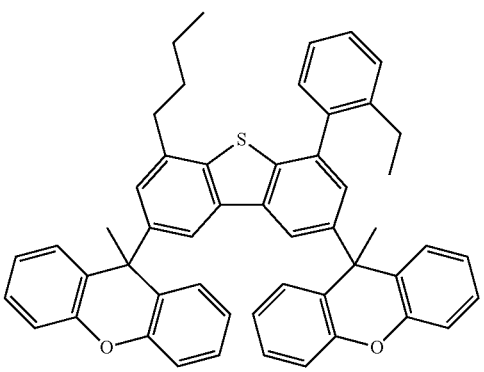
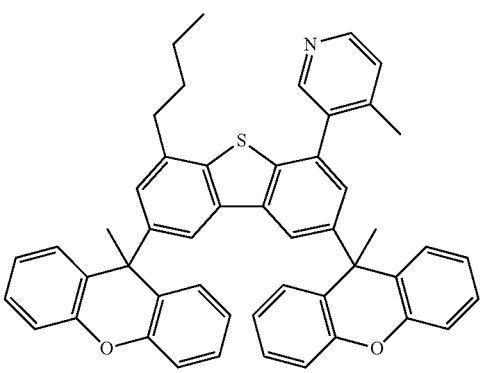

-continued
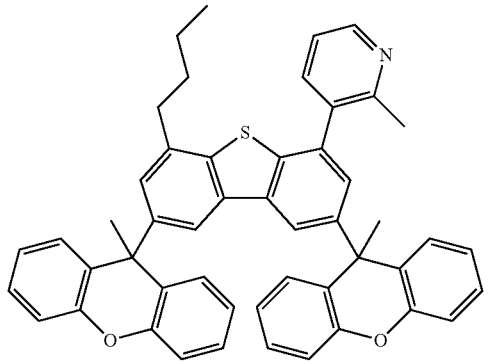
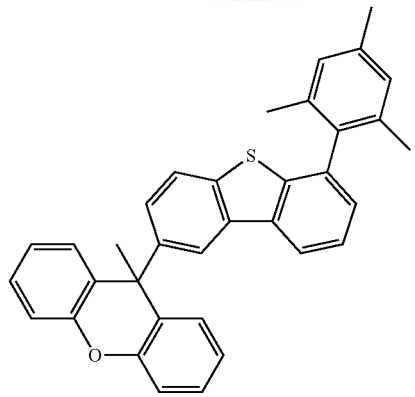
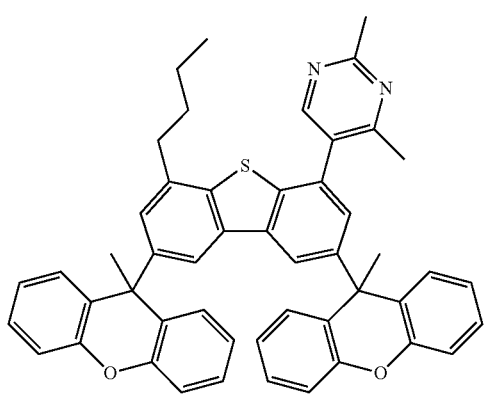
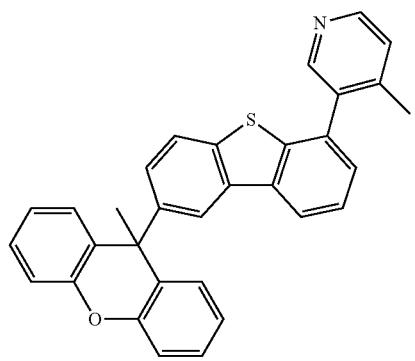
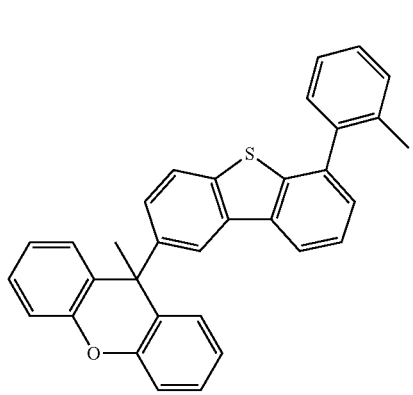
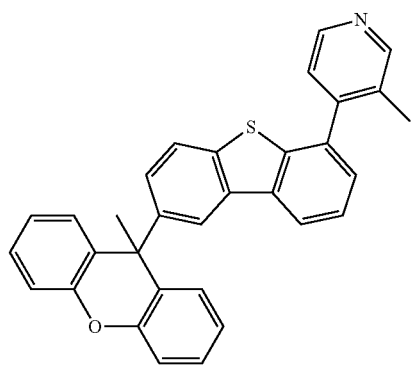
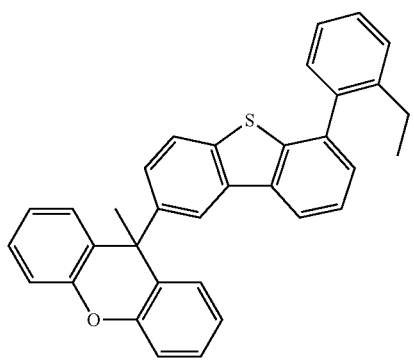
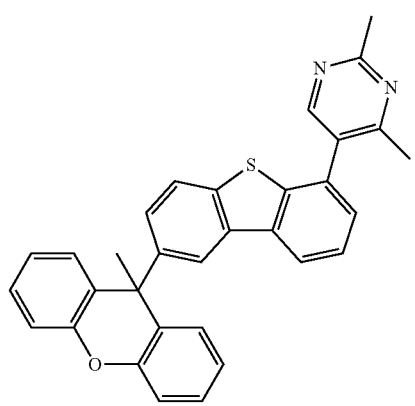

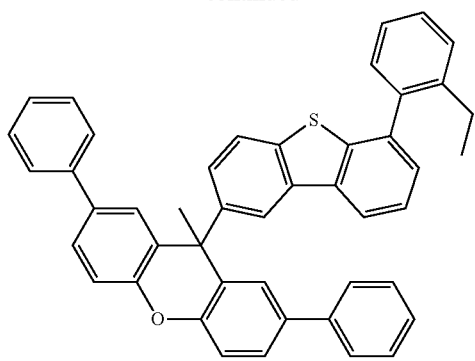
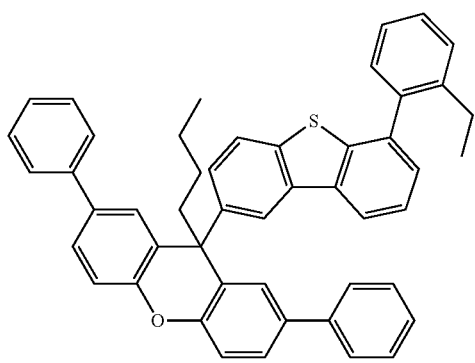
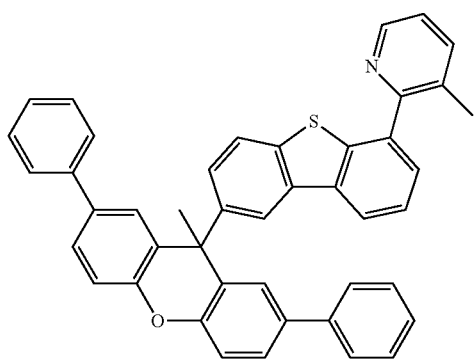
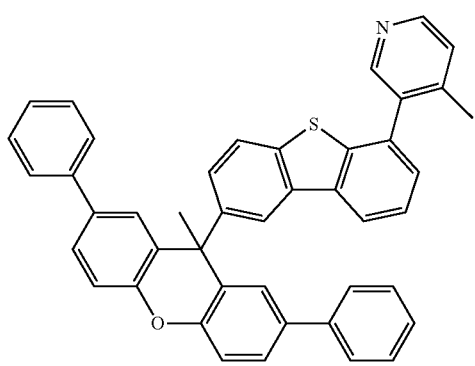
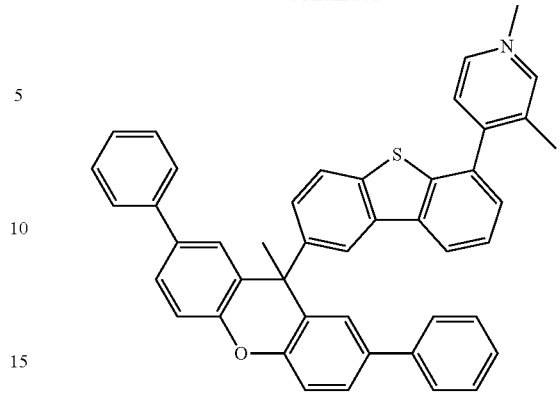
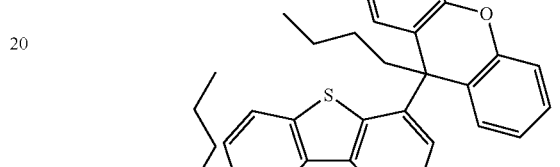
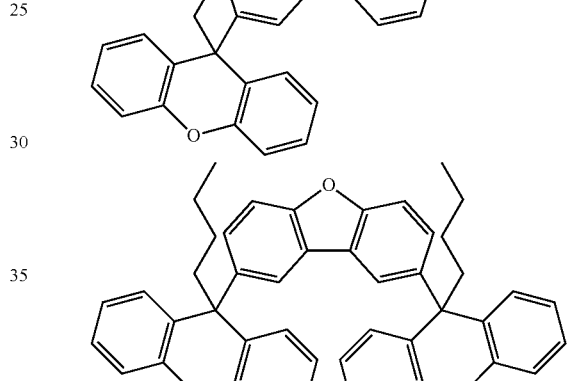
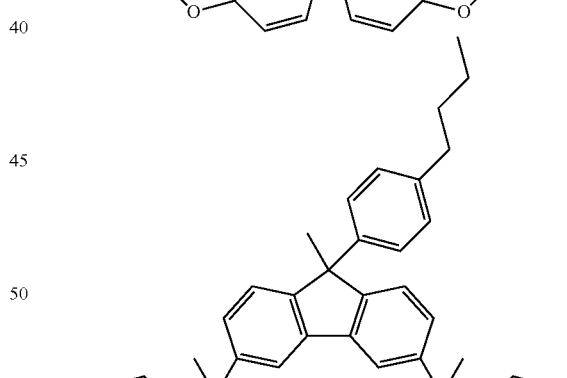
Light-Emitting Compounds
A preferred use of compounds of formula (I) is as the host material for a light-emitting material in a light-emitting layer of an OLED.
Suitable light-emitting materials for a light-emitting layer include polymeric, small molecule and dendritic light-emitting materials, each of which may be fluorescent or phosphorescent.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain more than one light-emitting material, for example a mixture of light-emitting materials that together provide white light emission.

A white-emitting OLED may contain a single, white-emitting layer or may contain two or more layers that emit different colours which, in combination, produce white light. The light emitted from a white-emitting OLED may have CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-6000K.

Exemplary phosphorescent light-emitting materials include metal complexes comprising substituted or unsubstituted complexes of formula (IX):

wherein M is a metal; each of $L^1$, $L^2$ and $L^3$ is a coordinating group; q is a positive integer; r and s are each independently 0 or a positive integer; and the sum of $(a \cdot q)+(b \cdot r)+(c \cdot s)$ is equal to the number of coordination sites available on M, wherein a is the number of coordination sites on $L^1$, b is the number of coordination sites on $L^2$ and c is the number of coordination sites on $L^3$. a, b and c are preferably each independently 1, 2 or 3. Preferably, a, b and c are each a bidentate ligand (a, b and c are each 2).

Heavy elements M induce strong spin-orbit coupling to allow rapid intersystem crossing and emission from triplet or higher states. Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Exemplary ligands $L^1$, $L^2$ and $L^3$ include carbon or nitrogen donors such as porphyrin or bidentate ligands of formula (X):

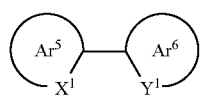

wherein $Ar^5$ and $Ar^6$ may be the same or different and are independently selected from substituted or unsubstituted aryl or heteroaryl; $X^1$ and $Y^1$ may be the same or different and are independently selected from carbon or nitrogen; and $Ar^5$ and $Ar^6$ may be fused together. Ligands wherein $X^1$ is carbon and $Y^1$ is nitrogen are preferred, in particular ligands in which $Ar^5$ is a single ring or fused heteroaromatic of N and C atoms only, for example pyridyl or isoquinoline, and $Ar^6$ is a single ring or fused aromatic, for example phenyl or naphthyl.

To achieve red emission, $Ar^5$ may be selected from phenyl, fluorene, naphthyl and $Ar^6$ are selected from quinoline, isoquinoline, thiophene and benzothiophene.

To achieve green emission, $Ar^5$ may be selected from phenyl or fluorene and $Ar^6$ may be pyridine.

To achieve blue emission, $Ar^5$ may be selected from phenyl and $Ar^6$ may be selected from imidazole, pyrazole, triazole and tetrazole.

Examples of bidentate ligands are illustrated below:

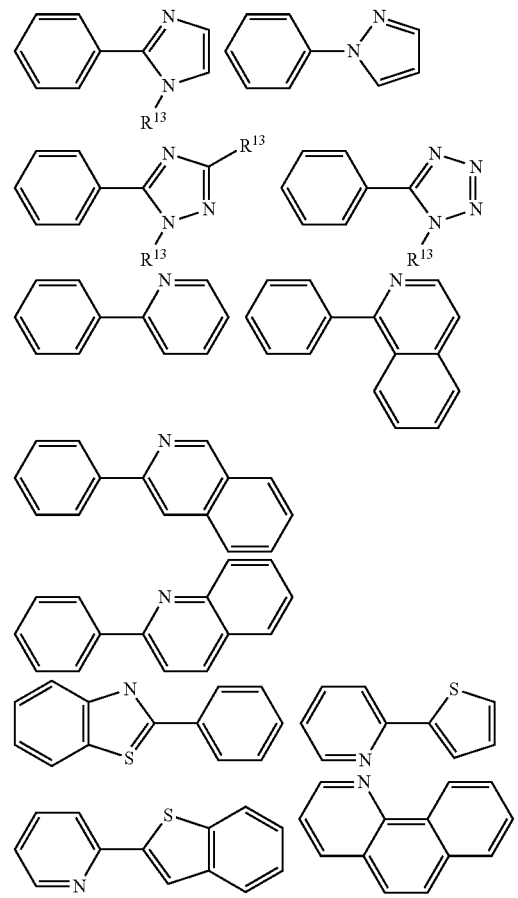

Each of $Ar^5$ and $Ar^6$ may carry one or more substituents. Two or more of these substituents may be linked to form a ring, for example an aromatic ring.

Other ligands suitable for use with d-block elements include diketonates, in particular acetylacetonate (acac), tetrakis-(pyrazol-1-yl)borate, 2-carboxypyridyl, triarylphosphines and pyridine, each of which may be substituted.

Exemplary substituents include groups $R^{13}$ as described below with reference to Formula (VII). Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example $C_{1-20}$ alkyl or alkoxy, which may be as disclosed in JP 2002-324679; carbazole which may be used to assist hole transport to the complex when used as an emissive material, for example as disclosed in WO 02/81448; and dendrons which may be used to obtain or enhance solution processability of the metal complex, for example as disclosed in WO 02/66552.

One or more of $L^1$, $L^2$ and $L^3$ may comprise a carbene group.

A light-emitting dendrimer comprises a light-emitting core bound to one or more dendrons, wherein each dendron comprises a branching point and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example alkyl or alkoxy.

A dendron may have optionally substituted formula (XI)

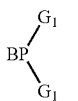
(XI)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (XIa):

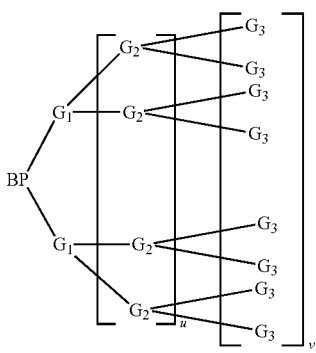
(XIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups. In one preferred embodiment, each of BP and $G_1$, $G_2$ . . . $G_n$ is phenyl, and each phenyl BP, $G_1$, $G_2$ . . . $G_{n-1}$ is a 3,5-linked phenyl.

A preferred dendron is a substituted or unsubstituted dendron of formula (XIb):

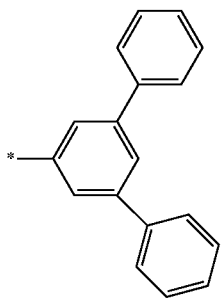
(XIb)

wherein * represents an attachment point of the dendron to a core.

BP and/or any group G may be substituted with one or more substituents, for example one or more $C_{1-20}$ alkyl or alkoxy groups.

Light-emitting material(s) in a composition comprising the compound of formula (I) and one or more light-emitting materials may make up about 0.05 wt % up to about 50 wt %, optionally about 1-40 wt % of the composition.

Charge Transporting and Charge Blocking Layers

A device containing a light-emitting layer containing a compound of formula (I) may have charge-transporting and/or charge blocking layers.

A hole transporting layer may be provided between the anode and the light-emitting layer or layers of an OLED. An electron transporting layer may be provided between the cathode and the light-emitting layer or layers.

An electron blocking layer may be provided between the anode and the light-emitting layer(s) and a hole blocking layer may be provided between the cathode and the light-emitting layer(s). Charge-transporting and charge-blocking layers may be used in combination. Depending on the HOMO and LUMO levels of the material or materials in a layer, a single layer may both transport one of holes and electrons and block the other of holes and electrons.

If present, a hole transporting layer located between the anode and the light-emitting layer(s) preferably has a material having a HOMO level of less than or equal to 5.5 eV, more preferably around 4.8-5.5 eV or 4.9-5.3 eV as measured by cyclic voltammetry. The HOMO level of the material in the hole transport layer may be selected so as to be within 0.2 eV, optionally within 0.1 eV of the light-emitting material of the light-emitting layer.

A hole-transporting layer may contain polymeric or non-polymeric charge-transporting materials. Exemplary hole-transporting materials contain arylamine groups.

A hole transporting layer may contain a homopolymer or copolymer comprising a repeat unit of formula (VII):

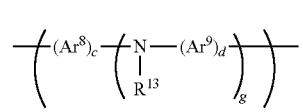
(VII)

wherein $Ar^8$ and $Ar^9$ in each occurrence are independently selected from substituted or unsubstituted aryl or heteroaryl, g is greater than or equal to 1, preferably 1 or 2, $R^{13}$ is H or a substituent, preferably a substituent, and c and d are each independently 1, 2 or 3.

$R^{13}$, which may be the same or different in each occurrence when g>1, is preferably selected from the group consisting of alkyl, for example $C_{1-20}$ alkyl, $Ar^{10}$, a branched or linear chain of $Ar^{10}$ groups, or a crosslinkable unit that is bound directly to the N atom of formula (VIII) or spaced apart therefrom by a spacer group, wherein $Ar^{10}$ in each occurrence is independently optionally substituted aryl or heteroaryl. Exemplary spacer groups are $C_{1-20}$ alkyl, phenyl and phenyl-$C_{1-20}$ alkyl.

Any of $Ar^8$, $Ar^9$ and, if present, $Ar^{10}$ in the repeat unit of Formula (VII) may be linked by a direct bond or a divalent linking atom or group to another of $Ar^8$, $Ar^9$ and $Ar^{10}$. Preferred divalent linking atoms and groups include O, S; substituted N; and substituted C.

Any of $Ar^8$, $Ar^9$ and, if present, $Ar^{10}$ may be substituted with one or more substituents. Exemplary substituents are substituents $R^{10}$, wherein each $R^{10}$ may independently be selected from the group consisting of:

substituted or unsubstituted alkyl, optionally $C_{1-20}$ alkyl, wherein one or more non-adjacent C atoms may be replaced with optionally substituted aryl or heteroaryl, O, S, substituted N, C=O or —COO— and one or more H atoms may be replaced with F; and
a crosslinkable group attached directly to the fluorene unit or spaced apart therefrom by a spacer group, for example a group comprising a double bond such and a vinyl or acrylate group, or a benzocyclobutane group Preferred repeat units of formula (VII) have formulae 1-3:

In one preferred arrangement, $R^{13}$ is $Ar^{10}$ and each of $Ar^8$, $Ar^9$ and $Ar^{10}$ are independently and optionally substituted with one or more $C_{1-20}$ alkyl groups. $Ar^8$, $Ar^9$ and $Ar^{10}$ are preferably phenyl.

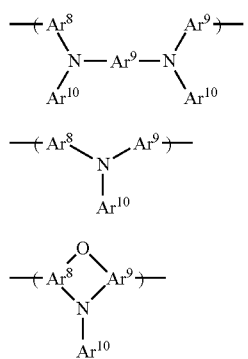

In another preferred arrangement, the central $Ar^9$ group of formula (1) linked to two N atoms is a polycyclic aromatic that may be unsubstituted or substituted with one or more substituents $R^{10}$. Exemplary polycyclic aromatic groups are naphthalene, perylene, anthracene and fluorene.

In another preferred arrangement, $Ar^8$ and $Ar^9$ are phenyl, each of which may be substituted with one or more $C_{1-20}$ alkyl groups, and $R^{13}$ is —$(Ar^{10})_r$ wherein r is at least 2 and wherein the group —$(Ar^{10})_r$ forms a linear or branched chain of aromatic or heteroaromatic groups, for example 3,5-diphenylbenzene wherein each phenyl may be substituted with one or more $C_{1-20}$ alkyl groups. In another preferred arrangement, c, d and g are each 1 and $Ar^8$ and $Ar^9$ are phenyl linked by an oxygen atom to form a phenoxazine ring.

A hole-transporting polymer containing repeat units of formula (VII) may be a copolymer containing one or more further repeat units. Exemplary further repeat units include arylene repeat units, each of which may be unsubstituted or substituted with one or more substituents. Exemplary arylene repeat units include fluorene, phenylene and dihydrophenanthrene repeat units, each of which may be unsubstituted or substituted with one or more substituents. Exemplary substituents of arylene repeat units, if present, may be selected from $C_{1-40}$ hydrocarbyl, preferably $C_{1-20}$ alkyl; phenyl; and phenyl-$C_{1-20}$ alkyl; and crosslinkable hydrocarbyl groups, for example $C_{1-40}$ hydrocarbyl groups comprising benzocyclobutene or vinylene groups.

If present, an electron transporting layer located between the light-emitting layers and cathode preferably has a LUMO level of around 1.8-2.7 eV as measured by cyclic voltammetry. An electron-transporting layer may have a thickness in the range of about 5-50 nm.

A charge-transporting layer or charge-blocking layer may be crosslinked, particularly if a layer overlying that charge-transporting or charge-blocking layer is deposited from a solution. The crosslinkable group used for this crosslinking may be a crosslinkable group comprising a reactive double bond such and a vinyl or acrylate group, or a benzocyclobutane group. The crosslinkable group may be provided as a substituent of, or may be mixed with, a charge-transporting or charge-blocking material used to form the charge-transporting or charge-blocking layer.

A charge-transporting layer adjacent to a light-emitting layer containing a phosphorescent light-emitting material preferably contains a charge-transporting material having a lowest triplet excited state ($T_1$) excited state that is no more than 0.1 eV lower than, preferably the same as or higher than, the $T_1$ excited state energy level of the phosphorescent light-emitting material(s) in order to avoid quenching of triplet excitons.

The polystyrene-equivalent number-average molecular weight (Mn) measured by gel permeation chromatography of the polymers described herein may be in the range of about $1 \times 10^3$ to $1 \times 10^8$, and preferably $1 \times 10^4$ to $5 \times 10^6$. The polystyrene-equivalent weight-average molecular weight (Mw) of the polymers described herein may be $1 \times 10^3$ to $1 \times 10^8$, and preferably $1 \times 10^4$ to $1 \times 10^7$.

Polymers as described herein are suitably amorphous.

Hole Injection Layers

A conductive hole injection layer, which may be formed from a conductive organic or inorganic material, may be provided between the anode 101 and the light-emitting layer 103 of an OLED as illustrated in the FIGURE to assist hole injection from the anode into the layer or layers of semiconducting polymer. Examples of doped organic hole injection materials include optionally substituted, doped poly (ethylene dioxythiophene) (PEDOT), in particular PEDOT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted polythiophene or poly(thienothiophene). Examples of conductive inorganic materials include transition metal oxides such as VOx, MoOx and RuOx as disclosed in Journal of Physics D: Applied Physics (1996), 29(11), 2750-2753.

Cathode

The cathode 105 is selected from materials that have a workfunction allowing injection of electrons into the light-emitting layer of the OLED. Other factors influence the selection of the cathode such as the possibility of adverse interactions between the cathode and the light-emitting material. The cathode may consist of a single material such as a layer of aluminium. Alternatively, it may comprise a plurality of conductive materials such as metals, for example a bilayer of a low workfunction material and a high workfunction material such as calcium and aluminium, for exampleas disclosed in WO 98/10621. The cathode may comprise elemental barium, for example as disclosed in WO 98/57381, Appl. Phys. Lett. 2002, 81(4), 634 and WO 02/84759. The cathode may comprise a thin (e.g. 1-5 nm) layer of metal compound, in particular an oxide or fluoride of an alkali or alkali earth metal, between the organic layers of the device and one or more conductive cathode layers to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

A formulation suitable for forming a charge-transporting or light-emitting layer may be formed from a compound of formula (I), any further components of the layer such as light-emitting dopants, and one or more suitable solvents.

The formulation may be a solution of the compound of formula (I) and any other components in the one or more solvents, or may be a dispersion in the one or more solvents in which one or more components are not dissolved. Preferably, the formulation is a solution.

Solvents suitable for dissolving compounds of formula (I), particularly compounds of formula (I) wherein one or more of $R^1$-$R^4$ comprises a $C_{1-20}$ alkyl group, are solvents comprising alkyl substituents for example benzenes substituted with one or more $C_{1-10}$ alkyl or $C_{1-10}$ alkoxy groups, for example toluene, xylenes and methylanisoles.

Particularly preferred solution deposition techniques including printing and coating techniques such spin-coating, inkjet printing and slot-die coating.

Spin-coating is particularly suitable for devices wherein patterning of the light-emitting layer is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

EXAMPLES

Example 1

Example 1 was prepared according to the following reaction scheme:

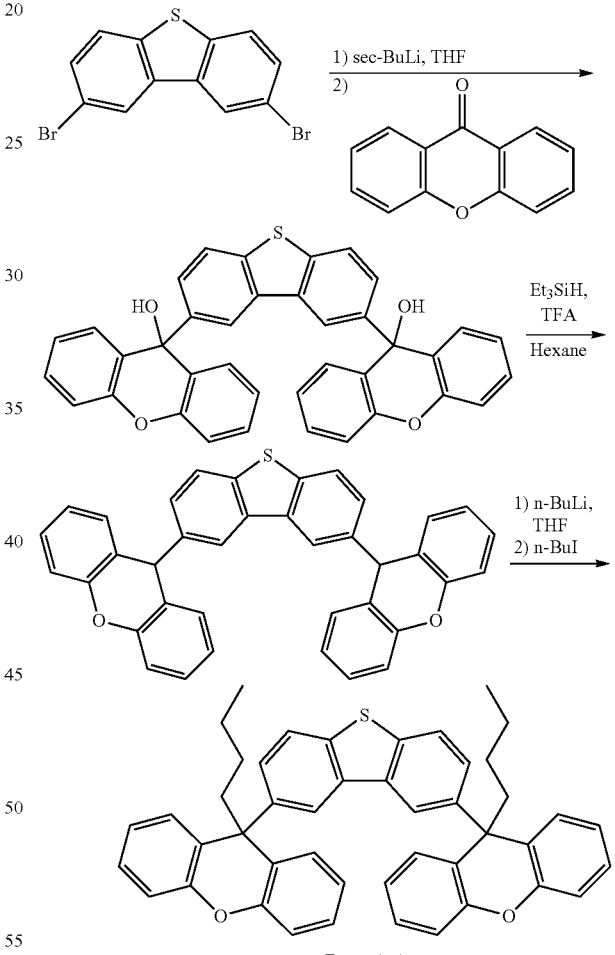

Example 1

2,8-Bis(9H-xanthen-9-ol-9-yl)-dibenzothiophene

To a slurry of 2,8-dibromodibenzothiophene (10.0 g, 29.2 mmol, 1 eq.) in 200 ml tetrahydrofuran at −78° C. was added drop wise 63 ml of sec-butyl lithium (1.4M in cyclohexane, 87.71 mmol, 3.0 eq.) such as internal temperature<−74° C. Xanthone (12.62 g, 64.32 mmol, 2.2 eq.) was added as a solid portion wise such as internal temperature<−74° C. Reaction mixture was allowed to warm up slowly to room temperature over night. Mixture was quenched by adding 50 ml of hydrochloric acid (2M aqueous) drop wise at 0° C. Tetrahydrofuran was removed under reduced pressure to give a solid in suspension in acidic solution. Solid was filtered and washed several time with water until water reached pH=7. Solid was triturated in 100 ml dichloromethane and filtered. It was then suspended in toluene and volatiles (azeotrope with water) were removed under reduced pressure to dryness. Resulting solid was dried over night in vacuum oven at 60° C. to give 13.9 g of 2,8-Bis(9H-xanthen-9-ol-9-yl)-dibenzothiophene (82% yield).

$^1$H NMR (600 MHz, THF-d8): δ (ppm)=6.02 (s, 2H), 6.99 (td, J=7.95 Hz, J=1.8 Hz, 4H), 7.09 (dd, J=8.44 Hz, J=1.77 Hz, 2H), 7.17 (dd, J=8.34 Hz, J=1.08 Hz, 4H), 7.25 (td, J=7.66 Hz, J=1.68 Hz, 4H), 7.40 (dd, J=7.92 Hz, J=1.56 Hz, 4H), 7.62 (d, J=8.46 Hz, 2H), 8.74 (d, J=1.50 Hz, 2H).

2,8-Bis(9H-xanthen-9-yl)-dibenzothiophene

To a suspension of 2,8-Bis(9H-xanthen-9-ol-9-yl)-dibenzothiophene (13.9 g, 24.1 mmol, 1 eq.) in 50 ml of hexane was added drop wise triethyl silane (8.0 ml, 49.4 mmol, 2.05 eq) followed by trifluoro acetic acid (17.9 ml, 241.0 mmol, 10.0 eq.) at 0° C. Extra hexane was added to ensure sufficient stirring. Mixture was allowed to warm up to room temperature and stirred for 2 hours.

Mixture was quenched by pouring it into 200 ml of ice/water. 100 ml of dichloromethane was added to dilute the organic phase and mixture was stirred for 1 hour at room temperature. Orange precipitate was formed; biphasic mixture was filtered on Buchner funnel, solid 1 and filtrate were kept separately. Phases from filtrate were separated and aqueous layer was extracted 3 times with dichloromethane. Combined organic phases were stirred for 20 minutes with 50 ml of potassium phosphate tribasic solution (10 wt % in water). Phases were separated and organic phase was washed 5 times with water, dried over MgSO$_4$ and reduced to dryness to give solid 2.

Solid 1 was triturated with potassium phosphate tribasic solution (10% wt in water) and filtered. It was washed several time with water until pH=6. It was then suspended in toluene and volatiles (azeotrope with water) were removed under reduced pressure to dryness. This step was repeated twice and the resulting pink solid was combined with solid 2.

Mixture of solids were dissolved in dichloromethane and adsorbed on Isolute®. It was dry loaded on top of a silica plug and eluted with a mixture of hexane:dichloromethane (1:1). Fractions containing product were combined and evaporated. The resulting white solid was triturated with methanol and filtered. It was then dried in vacuum oven at 60° C. over night to give 11.2 g of 2,8-Bis(9H-xanthen-9-yl)-dibenzothiophene (85% yield 99.85% pure by HPLC).

$^1$H NMR (600 MHz, CDCl$_3$): δ (ppm)=5.45 (s, 2H), 6.97 (td, J=7.47 Hz, J=1.2 Hz, 4H), 7.06 (d, J=7.32 Hz, 4H), 7.17 (dd, J=8.16 Hz, J=1.02 Hz, 4H), 7.23 (m, 6H), 7.71 (d, J=8.28 Hz, 2H), 8.03 (d, J=1.44 Hz, 2H).

2,8-Bis(9n-butyl-9H-xanthen-9-yl)-dibenzothiophene

To a suspension of 2,8-Bis(9H-xanthen-9-yl)-dibenzothiophene (3.8 g, 7.0 mmol, 1.0 eq.) in 80 ml of tetrahydrofuran at −78° C. was added drop wise n-butyl lithium (2.5M in hexane, 5.9 ml, 2.1 eq.) such as internal temperature<−74° C. Mixture was stirred for 2 hours at −78° C. then Mixture was allowed to warm up to 0° C. and stirred for 30 min at 0° C. Mixture was cooled down to −10° C. and n-butyl iodide was added drop wise to the mixture such as internal temperature<−5° C. Reaction mixture was allowed to warm up to room temperature over night.

It was quenched with 20 ml of water added drop wise at 0° C. Tetrahydrofuran was removed under reduced pressure. Biphasic residue was diluted with more water and dichloromethane was added to dissolve the solid. Phases were separated and aqueous layer was extracted once with dichloromethane. Combined organic phases were washed three times with water (until pH=7), dried over MgSO$_4$ and reduced to dryness. Residue was dissolved in a mixture of hexane:dichloromethane (1:1) and filtered through a silca/Florisil® plug (Florisil® layer on top of silica layer), eluted with in a mixture of hexane:dichloromethane (1:1). Fractions containing product were combined and evaporated under reduced pressure to give a white solid. 1.8 g of 2,8-Bis(9n-butyl-9H-xanthen-9-yl)-dibenzothiophene was purified by 6 successive recrystallisations in methanol/n-BuOAc to give 0.77 g of white solid (99.05% pure by HPLC).

$^1$H NMR (600 MHz, CDCl$_3$): δ (ppm)=0.80 (t, J=7.32 Hz, 6H), 1.01 (m, 4H), 1.28 (m, 4H), 2.45 (m, 4H), 6.84 (dd, J=7.86 Hz, J=1.5 Hz, 4H), 6.92 (td, J=7.44 Hz, J=1.26 Hz, 4H), 7.13 (dd, J=8.22 Hz, J=1.14 Hz, 4H), 7.19 (td, J=7.62 Hz, J=1.56 Hz, 4H), 7.24 (dd, J=8.52 Hz, J=1.8 Hzm 2H), 7.68 (d, J=8.52 Hz, 2H), 8.30 (d, J=1.62 Hz, 2H).

Phosphorescent Composition

A film of a composition of Blue Phosphorescent Emitter 1, 2 or 3 (5 wt %) and a host compound (95 wt %) of either Example 1 or Comparative Host 1 was formed by dissolving the composition and spin-casting the film.

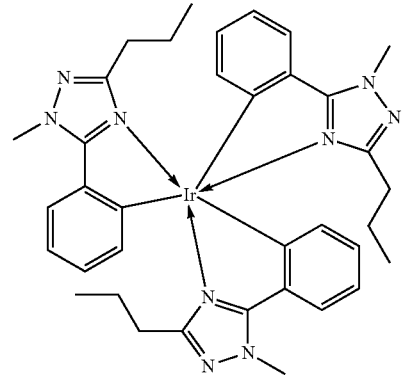

Blue Phosphorescent Emitter 1 (BPE1)

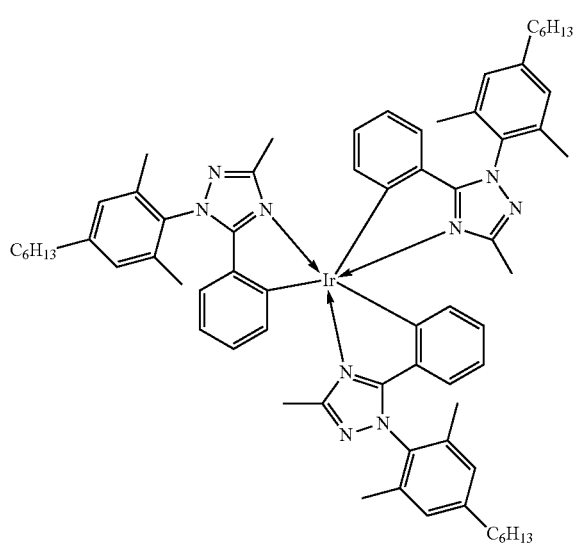

Blue Phosphorescent Emitter 2 (BPE2)

(BPE3)

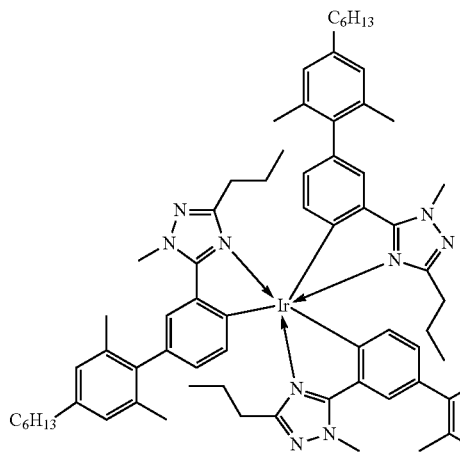

Blue Phosphorescent Emitter 3

Comparative Compound 1

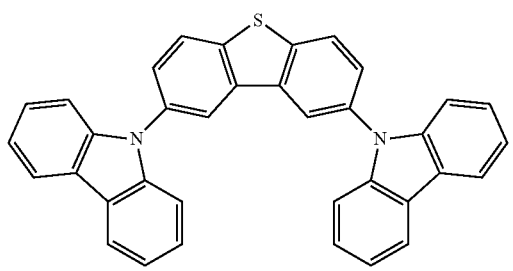

Example 1

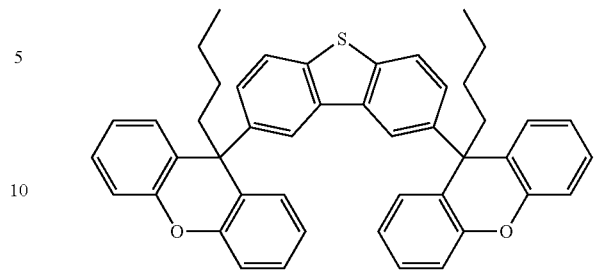

Photoluminescent properties of films prepared by this method are set out in Table 1.

Films were prepared by spin-coating the compositions from a solution in a solvent. Concentrations given in Table 1 is the total host+emitter weight per mg of the solvent.

The lowest triplet excited state ($T_1$) for an emitter given in Table 1 was derived from the half height of the peak in the photoluminescence spectrum of a composition containing that emitter.

Photoluminescent quantum yield (PLQY) was measured an integrating sphere, Hamamatsu, Model: C9920-02.

Transmittance range was between 0.30 and 0.40 for all samples. Transmittance range may be controlled by changing the spin speed or concentration.

For each sample the film was spun on a quartz substrate and placed in the integrating sphere. The sample is scaned with wavelengths 280 nm-350 nm approx and wavelength where the emission peak is the most intense is selected. A blank spectrum was measured at the chosen wavelength followed by measurement of the sample.

PLQY and CIE results in Table 1 are each an average of 3 results.

CIE x and CIE y values were measured using a Minolta CS200 ChromaMeter.

For each emitter, PLQY is higher for the composition containing Example 1.

TABLE 1

| Host | Emitter | Solvent | Sample conc. (mg/ml) | Excitation (nm) | PLQY (%) | CIE X | CIE Y | Emitter $T_1$ (eV) |
| --- | --- | --- | --- | --- | --- | --- | --- | --- |
| Example 1 | PBE1 | Xylene Mixed Isomers | 60 | 330 | 71.3 | 0.156 | 0.223 | 2.80 eV |
| Comparative Host 1 | PBE1 | Toluene | 20 | 340 | 59.0 | 0.158 | 0.227 | |
| Example 1 | PBE2 | Xylene Mixed Isomers | >50 | 330 | 78.7 | 0.152 | 0.219 | 2.77 eV |
| Comparative Host 1 | PBE2 | Toluene | 20 | 340 | 72.1 | 0.153 | 0.223 | |
| Example 1 | PBE3 | Xylene Mixed Isomers | >50 | 330 | 77.2 | 0.155 | 0.246 | 2.76 eV |
| Comparative Host 1 | PBE3 | Toluene | 20 | 340 | 69.6 | 0.158 | 0.252 | |

Energy Levels

Modeled energy levels of compounds of formula (I) and comparative compounds illustrated below are set out in Table 2. Energy levels were modeled using Gaussian software with TD-DFT calculations on DFT optimised structures, both using the B3LYP functional.

Comparative Compound 1 is disclosed in Sook et al, J. Mater. Chem., 2011, 21, 14604.

Comparative Compound 2 is disclosed in Organic Electronics 13 (2012) 2741-2746.

The $T_1$ level for Example Compounds 1, 2 and 3 are higher than that for either Comparative Compound 1 or 2.

Comparative Compound 1

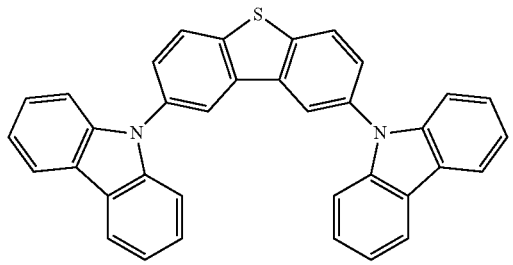

Comparative Compound 2

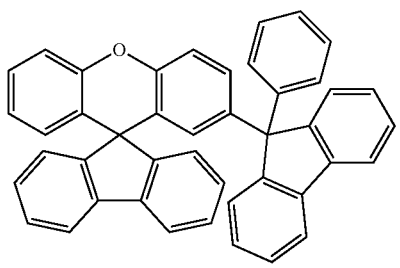

Example 1

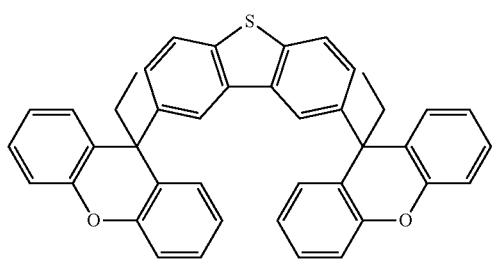

Example 2

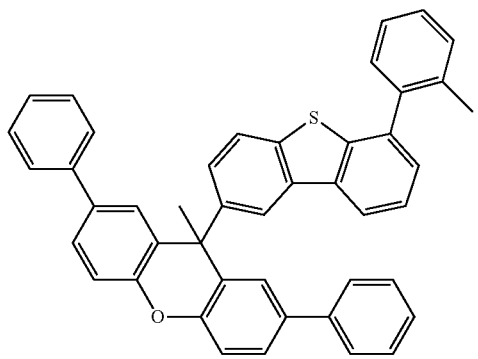

Example 3

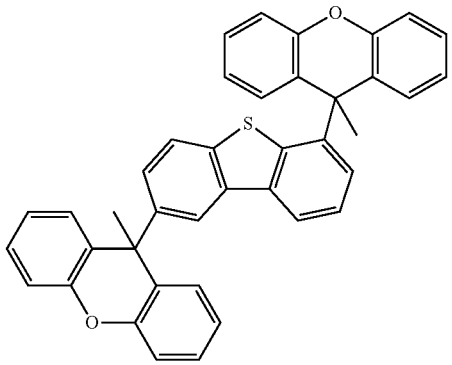

TABLE 2

| Compound | HOMO | LUMO | Eg | $T_1$ | $S_1$ |
| --- | --- | --- | --- | --- | --- |
| Comparative Compound 1 | −5.356 | −1.433 | 3.923 | 3.0809 | 3.3761 |
| Comparative Compound 2 | −5.545 | −0.87 | 4.674 | 3.03 | 3.9022 |
| Example 2 | −5.444 | −1.077 | 4.367 | 3.1125 | 3.8085 |
| Example 1 | −5.639 | −1.002 | 4.638 | 3.1263 | 3.7696 |
| Example 3 | −5.639 | −0.982 | 4.657 | 3.138 | 3.7868 |

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A composition consisting of a compound of formula (1) and at least one phosphorescent metal complex light-emitting dopant:

(I)

wherein:

n is 1;

Xan independently in each occurrence represents a group of formula (IIa):

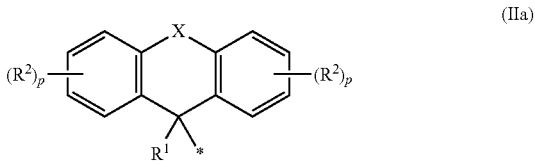
(IIa)

wherein X is O or S; $R^1$ independently in each occurrence is H or a substituent; $R^2$ independently in each occurrence is a substituent; p independently in each occurrence is 0, 1, 2, 3 or 4; and * represents a bond to $Ar^1$;

Ar¹ is a group of formula (IIIa):

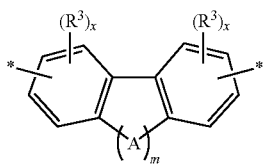

(IIIa)

wherein R³ is the same or different in each occurrence and is a substituent; x independently in each occurrence is 0, 1, 2 or 3; A independently in each occurrence is O or S; m is 1, 2 or 3; and * represents a point of attachment to a group Xan;

wherein the at least one phosphorescent metal complex light-emitting dopant comprises a phosphorescent metal complex light-emitting dopant having a photoluminescent spectrum with a peak in the range of 400-490 nm.

2. A composition according to claim 1, wherein the compound has formula (Ia):

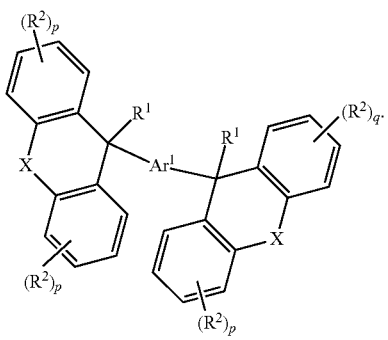

(Ia)

3. A formulation comprising a composition according to claim 1 and at least one solvent.

4. An organic light-emitting device comprising an anode, a cathode and one or more organic layers between the anode and cathode including a light-emitting layer wherein the organic light-emitting layer comprises a composition according to claim 1.

5. A method of forming an organic light-emitting device according to claim 4 comprising the step of forming the light-emitting layer over one of the anode and the cathode and forming the other of the anode and the cathode over the light-emitting layer.

6. A method according to claim 5 wherein the light-emitting layer is formed by depositing a formulation according to claim 3 and evaporating the at least one solvent.

7. A composition according to claim 1, wherein the at least one phosphorescent metal complex light-emitting dopant consists of a phosphorescent metal complex light-emitting dopant having a photoluminescent spectrum with a peak in the range of 400-490 nm.

8. A composition according to claim 1, wherein the phosphorescent metal complex has formula (IX):

$$ML^1_q L^2_r L^3_s \qquad (IX)$$

wherein M is a metal; each of $L^1$, $L^2$ and $L^3$ is a coordinating group; q is a positive integer; r and s are each independently 0 or a positive integer; and the sum of (a.q)+(b.r)+(c.s) is equal to the number of coordination sites available on M, wherein a is the number of coordination sites on $L^1$, b is the number of coordination sites on $L^2$ and c is the number of coordination sites on $L^3$.

9. A composition according to claim 8, wherein $L^1$ is phenylimidazole, phenylpyrazole, phenyltriazole, or phenyltetrazole, each of which may be unsubstituted or substituted with one or more substituents.

* * * * *